United States Patent
Turner et al.

(10) Patent No.: US 8,298,991 B2
(45) Date of Patent: Oct. 30, 2012

(54) METHOD FOR CONTROLLING UNDESIRED MIMOSOIDEAE VEGETATION

(75) Inventors: Ronnie Glenn Turner, Collierville, TN (US); Eric Paul Castner, Weatherford, TX (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/056,316

(22) PCT Filed: Jul. 28, 2009

(86) PCT No.: PCT/US2009/051928
§ 371 (c)(1),
(2), (4) Date: Jan. 28, 2011

(87) PCT Pub. No.: WO2010/019377
PCT Pub. Date: Feb. 18, 2010

(65) Prior Publication Data
US 2011/0136667 A1   Jun. 9, 2011

Related U.S. Application Data

(60) Provisional application No. 61/088,122, filed on Aug. 12, 2008.

(51) Int. Cl.
A01N 57/00 (2006.01)
A01N 43/40 (2006.01)
A01N 43/64 (2006.01)
A01N 43/30 (2006.01)

(52) U.S. Cl. ......... 504/128; 504/130; 504/134; 504/136

(58) Field of Classification Search .................. None
See application file for complete search history.

(56) References Cited

FOREIGN PATENT DOCUMENTS

WO 2005/063721 A1 7/2005
WO 2007/120706 A2 10/2007
WO WO 2007120706 * 10/2007

OTHER PUBLICATIONS

Bovey et al., Weed Science, 1985, "Herbicide Mixtures for Control of Honey Mesquite (Prosopis glandulosa)", vol. 33, pp. 349-352.
Creager, Weed Technology, 1992, "Seed Germination, Physical and Chemical Control of Catclaw Mimosa(Mimosa pigra var.pigra)", vol. 6, pp. 884-891.
Browne et al., Nov. 2004; "100 of the World's Worst Invasive Alien Species" A selection from the Global Invasive Species Database; pp. 1-12.

* cited by examiner

Primary Examiner — Alton Pryor

(57) ABSTRACT

Disclosed is method for controlling undesired vegetation of subfamily Mimosoideae comprising applying to the undesired vegetation or its environment a herbicidally effective amount of a mixture comprising (a) one or more compounds selected from the compound of Formula 1 and salts, esters and thioesters thereof:

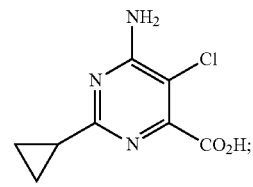

and
(b) at least one additional herbicide selected from the group consisting of
(b1) fosamine and salts thereof;
(b2) imazapyr and salts thereof;
(b3) metsulfuron-methyl and salts thereof; and
(b4) triclopyr and esters, thioesters and salts thereof.

8 Claims, No Drawings

METHOD FOR CONTROLLING UNDESIRED MIMOSOIDEAE VEGETATION

FIELD OF THE INVENTION

This invention relates to a method for controlling undesired vegetation of subfamily Mimosoideae by applying certain herbicidal mixtures.

BACKGROUND OF THE INVENTION

Mimosoideae is generally recognized as a major subfamily of the angiosperm plant family Fabaceae (alternatively named Leguminosae) and is characterized by flowers with small petals and numerous prominent stamens. Growth forms exhibited by Mimosoideae include trees, shrubs and, less frequently, lianas. Species of Mimosoideae are found in tropical, subtropical and warm temperate regions, to which they are well adapted. In common with members of Fabaceae, they generally form symbiotic relationships with nitrogen-fixing bacteria. Species of Mimosoideae serve as important sources of forage and fuel.

However, certain species of Mimosoideae can be undesirable competitors to plant species beneficial for agricultural and ranch operations. Such Mimosoideae species include huisache and certain mesquite species.

Species of mesquite for which control is often desired include *Prosopis glandulosa* and *P. velutina* in the sub-tropics and *P. juliflora* and *P. pallida* in the dry tropics. Although these species can grow into trees, they are most often shrub sized. Mesquite is well adapted to semiarid rangeland and pastures, because it can draw water from the water table through its long taproot. Mesquite can also draw water available in surface layers, thereby depriving desirable rangeland grasses of moisture. Even drawing water from the water table can be deleterious, as the proliferation of mesquite in parts of Texas is believed to be partly responsible for lowering groundwater levels ("Mesquite Becoming Thorny Water Issue for All of Texas", published by Office of Communications and Marketing of Angelo State University, San Angelo, Tex., released Jun. 19, 2001, available Jun. 19, 2009 from http://www.angelo.edu/services/communications marketing/archives/01jun/06-19-01.html). New growth of mesquite has needle-sharp thorns up to 75 mm long that are tough enough to penetrate rubber soles of shoes and even tires (http://en.wikipedia.org/wiki/Mesquite, Jun. 29, 2008). The mesquite species *P. glandulosa* has spread worldwide and is considered one of the world's worst invasive weeds ("100 of the World's Worst Invasive Alien Species", published by the Invasive Species Specialist Group of the Species Survival Commission of the World Conservation Union, November 2004, available Jun. 19, 2009 from http://www.issg.org/booklet.pdf).

Mechanically eradicating mesquite is difficult, because the plant's bud regeneration zone can extend 15 cm below ground level; mesquite can also regenerate from a piece of root ("Mesquite" article in Wikipedia as of Jun. 29, 2008, current version available from http://en.wikipedia.org/wiki/Mesquite). Furthermore, control of mesquite with conventional herbicides typically requires high application rates, and even then treatments are often ineffective or only partially effective against established mesquite. Defoliation may be followed by later regrowth. Typically monitoring for most of a year after herbicide treatment is necessary before the plants can be concluded to be completely dead.

Similar to mesquite, huisache (*Acacia farnesiana*) and certain other *Acacia* species are invasive, thorny, drought-tolerant trees and shrubs limiting forage in pastures and rangelands. Huisache occurs mainly in southwest Louisiana and southeast Texas in the U.S. Other *Acacia* species are of worldwide significance as weed pests. *A. drepanolobium* is considered an invasive savanna weed in parts of Africa. *A. karroo* is a problem in parts of Africa and Australia. *A. catechu* and *A. nilotica* present invasive threats to Australia. As for mesquite, eradication of established *Acacia* trees and shrubs using herbicides is often difficult, requiring high application rates, and even so, control is frequently incomplete.

PCT Patent Publication WO 2005/063721 discloses a new class of herbicidal pyrimidines, including 6-amino-5-chloro-2-cyclopropyl-4-pyrimidinecarboxylic acid, its esters, thioesters and salts. Although these herbicides have been subsequently found to exhibit herbicidal activity against undesired vegetation in the subfamily Mimosoideae such as *Acacia* and *Prosopis* species, their efficacy at relatively low application rates is not always sufficient for satisfactory control of these weeds. Mixtures with certain other herbicides have now been discovered to provide remarkable efficacy, thus affording a particularly useful method for controlling these weeds.

SUMMARY OF THE INVENTION

This invention pertains to a method for controlling undesired vegetation of subfamily Mimosoideae comprising applying to the undesired vegetation or its environment a herbicidally effective amount of a mixture comprising (a) one or more compounds selected from the compound of Formula 1 and salts, esters and thioesters thereof:

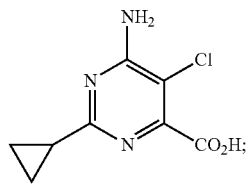

and
(b) at least one additional herbicide selected from the group consisting of
(b1) fosamine and salts thereof;
(b2) imazapyr and salts thereof;
(b3) metsulfuron-methyl and salts thereof; and
(b4) triclopyr and esters, thioesters and salts thereof.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, or method that comprises a list of elements is not necessarily limited to only those elements but may include other elements not expressly listed or inherent to such composition, mixture, process, or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

In recitations herein, the term "alkyl", used either alone or in compound words such as "alkoxyalkyl" or "hydroxyalkyl" includes straight-chain or branched alkyl, such as, methyl, ethyl, n-propyl, i-propyl, or the different butyl, pentyl or hexyl isomers. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkylthio" includes branched or straight-chain alkylthio moieties such as methylthio, ethylthio, and the different propylthio, butylthio, pentylthio and hexylthio isomers. An "alkylthiol" has a hydrogen atom bonded to the sulfur atom of "alkylthio". Carbon atoms in a substituent group is indicated by the "$C_i$-$C_j$" prefix where i and j are, for example, numbers from 1 to 14. For example, $C_2$ alkoxyalkyl designates $CH_3OCH_2$—; $C_3$ alkoxyalkyl designates, for example, $CH_3CH(OCH_3)$—, $CH_3OCH_2CH_2$— or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

As is generally understood in the art, the term "oil" refers to a slippery or viscous liquid not miscible with water. In the context of the present invention, the term "oil" more particularly relates to an organic chemical compound or mixture of compounds that is liquid at 20° C. and is soluble in water to an extent less than about 2% by weight at 20° C. Examples of oils include mineral oils, other liquid petroleum fractions (e.g., diesel fuel oil), vegetable oils (i.e. oils obtained from seeds and fruits) and methylated seed oils (e.g., methylated soybean oil, methylated rapeseed oil), including mixtures thereof.

As referred to herein, "Mimosoideae" is a subfamily of the plant family Fabaceae and includes five tribes: Acacieae (including the genera *Acacia* (including new genera resulting from taxonomic reclassification) and *Faidherbia*), Ingeae (including the genera *Abarema, Albizia, Archidendron, Archidendropsis, Balizia, Blanchetiodendron, Calliandra, Cathormion, Cedrelinga, Chloroleucon, Cojoba, Ebenopsis, Enterolobium, Falcataria, Guinetia, Havardia, Hesperalbizia, Hydrochorea, Inga, Lebekia, Leucochloron, Lysiloma, Macrosamanea, Painteria, Parachidendron, Paraserianthes, Pithecellobium, Pseudosamanea, Samanea, Serianthes, Sphinga, Wallaceodendron, Zapoteca* and *Zygia*), Mimoseae (including the genera *Adenanthera, Adenopodia, Alantsilodendron, Amblygonocarpus, Anadenanthera, Aubrevillea, Calliandropsis, Calpocalyx, Cylicodiscus, Desmanthus, Dichrostachys, Elephantorrhiza, Entada, Fillaeopsis, Gagnebina, Indopiptadenia, Kanaloa, Lemurodendron, Leucaena, Microlobius, Mimosa, Neptunia, Newtonia, Parapiptadenia, Piptadenia, Piptadeniastrum, Piptadeniopsis, Plathymenia, Prosopidastrum, Prosopis, Pseudopiptadenia, Pseudoprosopis, Schleinitzia, Stryphnodendron, Tetrapleura, Xerocladia* and *Xylia*), Mimozygantheae (including the genus *Mimozyganthus*), and Parkieae (including the genera *Parkia* and *Pentaclethra*).

As referred to herein "mesquite" includes species of the genus *Prosopis* L. Species of mesquite for which control is often desired include *P. glandulosa* Torr. (honey mesquite), *P. juliflora* (Sw.) DC. (mesquite), *P. pallida* (Humb. & Bonpl. ex Willd.) Kunth (kiawe) and *P. velutina* Woot. (velvet mesquite). Examples of additional *Prosopis* species for which control may be desired include *P. africana* (Guill., Perr. & A. Rich.) Taubert (African mesquite), *P. alba* Griseb. (algarrobo blanco), *P. alpataco* Phil., *P. argentine* Burkart, *P. burkartii* Muñoz, *P. caldenia* Burkart, *P. calingastana* Burkart (cusqui), *P. campestris* Griseb., *P. castellanosii* Burkart, *P. chilensis* (Molina) Stuntz (algarrobo), *P. cineraria* (L.) Druce (jand), *P. denudans* Benth., *P. elata* (Burkart) Burkart, *P. farcta* (Banks & Sol.) J. F. Macbr. (Syrian mesquite), *P. ferox* Griseb., *P. fiebrigii* Harms, *P. hassleri* Harms ex Hassler, *P. humulis* Gillies ex Hook. & Am., *P. kuntzei* Harms ex Hassler, *P. laevigata* (Humb. & Bonpl. ex Willd.) M. C. Johnst (smooth mesquite), *P. nigra* Griseb. ex Hieron. (algarrobo negro), *P. palmeri* S. Watson, *P. pubescens* Benth. (screwbean mesquite), *P. reptans* Benth. (tornillo), *P. rojasiana* Burkart, *P. ruizlealii* Burkart, *P. ruscifolia* Griseb., *P. sericantha* Gillies ex Hook. & Arn., *P. strombulifera* (Lam.) Benth. (Argentine screwbean), *P. tamarugo* F. Philippi (tamarugo) and *P. torquata* DC.

"Huisache", also known commonly as "sweet acacia", has the botanical name *Acacia farnesiana* (L.) Willd. Other species of the genus *Acacia* Mill. that are often considered invasive weeds deleterious to rangeland include: *A. catechu* (L. f.) Willd. (cutch tree), *A. drepanolobium* Harms ex Y. Sjostedt (whistling thorn), *A. karroo* Hayne (sweet thorn, Karroo thorn) and *A. nilotica* (L.) Willd. ex Delile (gum arabic tree, prickly acacia).

Embodiments of the Present Invention Include:

Embodiment A1. The method described in the Summary of the Invention wherein component (a) (i.e. one or more compounds selected from the compound of Formula 1 and salts, esters and thioesters thereof) is selected from esters and salts of the compound of Formula 1.

Embodiment A2. The method described in the Summary of the Invention wherein component (a) is selected from esters of the compound of Formula 1.

Embodiment A3. The method described in the Summary of the Invention or Embodiment A1 or A2 wherein the esters of the compound of Formula 1 are selected from $C_1$-$C_{14}$ alkyl, $C_2$-$C_{14}$ alkoxyalkyl, $C_3$-$C_{14}$ alkoxyalkoxyalkyl, $C_2$-$C_{14}$ hydroxyalkyl and benzyl esters of the compound of Formula 1.

Embodiment A4. The method of Embodiment A3 wherein the esters of the compound of Formula 1 are selected from $C_1$-$C_4$ alkyl esters of the compound of Formula 1.

Embodiment A5. The method of Embodiment A4 wherein the esters of the compound of Formula 1 are selected from $C_1$-$C_2$ alkyl esters of the compound of Formula 1.

Embodiment A6. The method of any one of Embodiments A1 through A5 wherein component (a) comprises the methyl ester of the compound of Formula 1.

Embodiment A7. The method of Embodiment A6 wherein component (a) is the methyl ester of the compound of Formula 1.

Embodiment A8. The method of Embodiment A1 wherein component (a) is selected from salts of the compound of Formula 1.

Embodiment A9. The method described in the Summary of the Invention or Embodiment A1 or A8 wherein the salts of the compound of Formula 1 are selected from ammonia (i.e. ammonium), amine (i.e. ammonium substituted with carbon-based substituents) and alkali metal salts of the compound of Formula 1.

Embodiment A10. The method of Embodiment A9 wherein the salts of the compound of Formula 1 are selected from the ammonium, dimethylammonium and isopropylammonium salts of the compound of Formula 1.

Embodiment A11. The method of Embodiment A9 wherein the salts of the compound of Formula 1 are selected from the lithium, sodium and potassium salts of the compound of Formula 1.

Embodiment A12. The method of Embodiment A11 wherein the salts of the compound of Formula 1 are selected from the sodium and potassium salts of the compound of Formula 1.

Embodiment A13. The method of any one of Embodiments A1, A8, A9, A11 and A12 wherein component (a) comprises the potassium salt of the compound of Formula 1.

Embodiment A14. The method of Embodiment A13 wherein component (a) is the potassium salt of the compound of Formula 1.

Embodiment B1. The method described in the Summary of the Invention or any one of Embodiments A1 through A14 wherein component (b) (i.e. the at least one additional herbicide) is selected from the group consisting of (b1) fosamine and salts thereof; (b2) imazapyr and salts thereof; (b3) metsulfuron-methyl and salts thereof; and (b4) triclopyr and esters, thioesters and salts thereof.

Embodiment B2. The method of Embodiment B1 wherein at least one herbicide of component (b) is selected from (b2), (b3) and (b4).

Embodiment B3. The method of Embodiment B1 wherein at least one herbicide of component (b) is selected from (b1), (b3) and (b4).

Embodiment B4. The method of Embodiment B1 wherein at least one herbicide of component (b) is selected from (b1), (b2) and (b4).

Embodiment B5. The method of Embodiment B1 wherein at least one herbicide of component (b) is selected from (b1), (b2) and (b3).

Embodiment B6. The method of Embodiment B1 wherein at least one herbicide of component (b) is selected from (b1).

Embodiment B7. The method of Embodiment B1 wherein at least one herbicide of component (b) is selected from (b2).

Embodiment B8. The method of Embodiment B1 wherein at least one herbicide of component (b) is selected from (b3).

Embodiment B9. The method of Embodiment B1 wherein at least one herbicide of component (b) is selected from (b4).

Embodiment B10. The method of any one of Embodiments B1 through B9 wherein the only herbicidally active ingredients in the mixture are selected from components (a) and (b).

Embodiment B11. The method of any one of Embodiments B1, and B3 through B6 wherein the only herbicidally active ingredients in the mixture are selected from components (a) and (b1).

Embodiment B12. The method of any one of Embodiments B1, B2, B4, B5 and B7 wherein the only herbicidally active ingredients in the mixture are selected from components (a) and (b2).

Embodiment B13. The method of any one of Embodiments B1 through B3, B5 and B8 wherein the only herbicidally active ingredients in the mixture are selected from components (a) and (b3).

Embodiment B14. The method of any one of Embodiments B1 through B4, and B9 wherein the only herbicidally active ingredients in the mixture are selected from components (a) and (b4).

Embodiment B15. The method of any one of Embodiments B1, B3 through B6, B10 and B11 wherein (b1) is selected from salts of fosamine.

Embodiment B16. The method of Embodiment B15 wherein (b1) is the ammonium salt of fosamine (i.e. fosamine-ammonium).

Embodiment B17. The method of any one of Embodiments B1, B2, B4, B5, B7, B10 and B12 wherein (b2) is selected from salts of imazapyr.

Embodiment B18. The method of Embodiment B17 wherein (b2) is the isopropylammonium salt of imazapyr (i.e. imazapyr-isopropylammonium).

Embodiment B19. The method of any one of Embodiments B1 through B3, B5, B8, B10 and B13 wherein (b3) is selected from metsulfuron-methyl (i.e. free acid form of metsulfuron-methyl) and the sodium and potassium salts of metsulfuron-methyl.

Embodiment B20. The method of Embodiment B19 wherein (b3) is metsulfuron-methyl.

Embodiment B21. The method of any one of Embodiments B1 through B4, B9, B10 and B14 wherein (b4) is selected from esters and salts of triclopyr.

Embodiment B22. The method of Embodiment B21 wherein (b4) is selected from $C_1$-$C_{12}$ alkyl esters and $C_2$-$C_{12}$ alkoxyalkyl esters of triclopyr.

Embodiment B23. The method of Embodiment B22 wherein (b4) is selected from $C_3$-$C_8$ alkoxyalkyl esters of triclopyr.

Embodiment B24. The method of Embodiment B23 wherein (b4) is the 2-butoxyethyl ester of triclopyr (i.e. triclopyr-butotyl).

Embodiment B25. The method of Embodiment B21 wherein (b4) is selected from ammonia (i.e. ammonium), amine (i.e. ammonium substituted with carbon-based substituents) and alkali metal salts of triclopyr.

Embodiment B26.

The method of Embodiment B25 wherein (b4) is the triethylammonium salt of triclopyr (i.e. triclopyr-triethylammonium).

Embodiment C1. The method described in the Summary of Invention or any one of Embodiments A1 through A14 and B1 through B26 wherein the undesired vegetation of subfamily Mimosoideae comprises at least one species of genus *Prosopis*.

Embodiment C2. The method of Embodiment C1 wherein the undesired vegetation comprises at least one species selected from *Prosopis glandulosa, P. velutina, P. juliflora* and *P. pallida*.

Embodiment C3. The method of Embodiment C2 wherein the undesired vegetation comprises at least one species selected from *Prosopis glandulosa* and *P. velutina*.

Embodiment C4. The method of Embodiment C3 wherein the undesired vegetation comprises *P. glandulosa*.

Embodiment C5. The method described in the Summary of the Invention or any one of Embodiments A1 through A14, B1 through B26, and C1 through C4 wherein the undesired vegetation of subfamily Mimosoideae comprises at least one species of genus *Acacia*.

Embodiment C6. The method of Embodiment C5 wherein the undesired vegetation comprises at least one species selected from *Acacia farnesiana, A. drepanolobium, A. karroo, A. catechu* and *A. nilotica*.

Embodiment C7. The method of Embodiment C6 wherein the undesired vegetation comprises *Acacia* farnesiana.

Embodiment D1. The method described in the Summary of the Invention or any one of Embodiments A1 through A14, B1 through B26, and C1 through C7 wherein the undesired vegetation has foliage.

Embodiment D2. The method of Embodiment D1 wherein a herbicidally effective amount of the mixture comprising components (a) and (b) is applied to the foliage of the undesired vegetation.

Embodiment D3. The method described in the Summary of the Invention or any one of Embodiments A1 through A14, B1 through B26, C1 through C7, and D1 through D2 wherein the mixture comprising components (a) and (b) is applied in a spray composition further comprising at least 0.1 percent by volume of an oil.

Embodiment D4. The method of Embodiment D1 wherein the spray composition comprises no more than about 5 percent by volume of the oil.

Embodiment D5. The method of Embodiment D3 or D4 wherein the oil comprises at least one oil selected from vegetable oils and methylated seed oils (including mixtures thereof).

Embodiment D6. The method of Embodiment D5 wherein the oil comprises at least one oil selected from methylated seed oils.

Embodiment D7. The method described in the Summary of the Invention or any one of Embodiments A1 through A14, B1 through B26, C1 through C7, and D1 through D6 wherein the undesired vegetation is at least about 1 year old.

Embodiment D8. The method of Embodiment D7 wherein the undesired vegetation is at least about 5 years old.

Embodiment D9. The method of Embodiment D8 wherein the undesired vegetation is at least about 10 years old.

Embodiment E1. The method described in the Summary of the Invention or any one of Embodiments A1 through A14, B1 through B26, C1 through C7, and D1 through D9 wherein component (a) in the mixture is applied at an application rate not exceeding about 600 g a.e. (acid equivalent, i.e. based on the Formula 1 acid) per hectare.

Embodiment E2. The method of Embodiment E1 wherein component (a) is applied at an application rate not exceeding about 300 g a.e. per hectare.

Embodiment E3. The method described in the Summary of the Invention or any one of Embodiments A1 through A14, B1 through B26, C1 through C7, D1 through D9 and E1 through E2 wherein component (a) in the mixture is applied at an application rate of at least about 50 g a.e. per hectare.

Embodiment E4. The method of Embodiment E3 wherein component (a) in the mixture is applied at an application rate of at least about 100 g a.e. per hectare.

Embodiment F1. The method described in the Summary of the Invention or any one of Embodiments A1 through A14, B1 through B26, C1 through C7, D1 through D9, and E1 through E4 wherein the weight ratio of component (b1) based on fosamine to component (a) based on the Formula 1 acid is at least about 14:1.

Embodiment F2. The method of Embodiment F1 wherein the weight ratio of component (b1) based on fosamine to component (a) based on the Formula 1 acid is at least about 20:1.

Embodiment F3. The method of Embodiment F2 wherein the weight ratio of component (b1) based on fosamine to component (a) based on the Formula 1 acid is at least about 22:1.

Embodiment F4. The method described in the Summary of the Invention or any one of Embodiments A1 through A14, B1 through B26, C1 through C7, D1 through D9, E1 through E4, and F1 through F3 wherein the weight ratio of component (b1) based on fosamine to component (a) based on the Formula 1 acid is no more than about 45:1.

Embodiment F5. The method of Embodiment F4 wherein the weight ratio of component (b1) based on fosamine to component (a) based on the Formula 1 acid is no more than about 36:1.

Embodiment F6. The method of Embodiment F5 wherein the weight ratio of component (b1) based on fosamine to component (a) based on the Formula 1 acid is no more than about 32:1.

Embodiment F7. The method described in the Summary of the Invention or any one of Embodiments A1 through A14, B1 through B26, C1 through C7, D1 through D9, E1 through E4, and F1 through F6 wherein the weight ratio of component (b2) based on imazapyr to component (a) based on the Formula 1 acid is at least about 0.2:1.

Embodiment F8. The method of Embodiment F7 wherein the weight ratio of component (b2) based on imazapyr to component (a) based on the Formula 1 acid is at least about 0.8:1.

Embodiment F9. The method of Embodiment F8 wherein the weight ratio of component (b2) based on imazapyr to component (a) based on the Formula 1 acid is at least about 1:1.

Embodiment F10. The method described in the Summary of the Invention or any one of Embodiments A1 through A14, B1 through B26, C1 through C7, D1 through D9, E1 through E4, and F1 through F9 wherein the weight ratio of component (b2) based on imazapyr to component (a) based on the Formula 1 acid is no more than about 2.4:1.

Embodiment F11. The method of Embodiment F10 wherein the weight ratio of component (b2) based on imazapyr to component (a) based on the Formula 1 acid is no more than about 1.8:1.

Embodiment F12. The method of Embodiment F11 wherein the weight ratio of component (b2) based on imazapyr to component (a) based on the Formula 1 acid is no more than about 1.6:1.

Embodiment F13. The method described in the Summary of the Invention or any one of Embodiments A1 through A14, B1 through B26, C1 through C7, D1 through D9, E1 through E4, and F1 through F12 wherein the weight ratio of component (b3) based on metsulfuron-methyl to component (a) based on the Formula 1 acid is at least about 0.03:1.

Embodiment F14. The method of Embodiment F13 wherein the weight ratio of component (b3) based on metsulfuron-methyl to component (a) based on the Formula 1 acid is at least about 0.1:1.

Embodiment F15. The method of Embodiment F14 wherein the weight ratio of component (b3) based on metsulfuron-methyl to component (a) based on the Formula 1 acid is at least about 0.15:1.

Embodiment F16. The method described in the Summary of the Invention or any one of Embodiments A1 through A14, B1 through B26, C1 through C7, D1 through D9, E1 through E4, and F1 through F15 wherein the weight ratio of component (b3) based on metsulfuron-methyl to component (a) based on the Formula 1 acid is no more than about 0.4:1.

Embodiment F17. The method of Embodiment F16 wherein the weight ratio of component (b3) based on metsulfuron-methyl to component (a) based on the Formula 1 acid is no more than about 0.3:1.

Embodiment F18. The method of Embodiment F17 wherein the weight ratio of component (b3) based on metsulfuron-methyl to component (a) based on the Formula 1 acid is no more than about 0.22:1.

Embodiment F19. The method described in the Summary of the Invention or any one of Embodiments A1 through A14, B1 through B26, C1 through C7, D1 through D9, E1 through E4, and F1 through F18 wherein the weight ratio of component (b4) based on triclopyr to component (a) based on the Formula 1 acid is at least about 0.8:1.

Embodiment F20. The method of Embodiment F19 wherein the weight ratio of component (b4) based on triclopyr to component (a) based on the Formula 1 acid is at least about 1.6:1.

Embodiment F21. The method of Embodiment F20 wherein the weight ratio of component (b4) based on triclopyr to component (a) based on the Formula 1 acid is at least about 2:1.

Embodiment F22. The method described in the Summary of the Invention or any one of Embodiments A1 through A14, B1 through B26, C1 through C7, D1 through D9, E1 through E4, and F1 through F21 wherein the weight ratio of component (b4) based on triclopyr to component (a) based on the Formula 1 acid is no more than about 4:1.

Embodiment F23. The method of Embodiment F22 wherein the weight ratio of component (b4) based on triclopyr to component (a) based on the Formula 1 acid is no more than about 3.2:1.

Embodiment F24. The method of Embodiment F23 wherein the weight ratio of component (b4) based on triclopyr to component (a) based on the Formula 1 acid is no more than about 2.8:1.

Embodiments of this invention, including Embodiments A1-F24 above as well as any other embodiments described herein, can be combined in any manner.

The present method for controlling undesired vegetation of subfamily Mimosoideae involves applying a herbicidally effective amount of a mixture comprising (a) one or more compounds selected from the compound of Formula 1 (6-amino-5-chloro-2-cyclopropyl-4-pyrimidinecarboxylic acid) and salts, esters and thioesters thereof; and (b) at least one additional herbicide selected from the group consisting of (b1) fosamine and salts thereof; (b2) imazapyr and salts thereof; (b3) metsulfuron-methyl and salts thereof; and (b4) triclopyr and salts, esters and thioesters thereof. Although the compound of Formula 1 and salts, ester and thioesters thereof are highly active defoliants of Mimosoideae vegetation, eventual regrowth of established plants can occur when these herbicides are used at relatively low application rates. Remarkably mixtures with fosamine, imazapyr, metsulfuron-methyl and/or triclopyr (including their salt, ester and thioester derivatives) have been discovered to synergistically prevent regrowth and permanently kill Mimosoideae vegetation. Therefore an aspect of the present invention is a method for controlling undesired vegetation of subfamily Mimosoideae comprising applying to the undesired vegetation or its environment a herbicidally effective amount of a mixture comprising synergistic amounts of (a) one or more compounds selected from the compound of Formula 1 and salts, esters and thioesters thereof; and (b) at least one additional herbicide selected from the group consisting of (b1) fosamine and salts thereof; (b2) imazapyr and salts thereof; (b3) metsulfuron-methyl and salts thereof; and (b4) triclopyr and esters, thioesters and salts thereof.

As already mentioned, the compound of Formula 1, fosamine, imazapyr, metsulfuron-methyl and triclopyr can be used in the present method as their salts. One skilled in the art recognizes that in the environment and under physiological conditions salts of these compounds are in equilibrium with their nonsalt forms, and therefore a salt shares the biological utility of the nonsalt form. Thus a wide variety of salts of the compound of Formula 1, fosamine, imazapyr, metsulfuron-methyl and triclopyr are useful for control of undesired vegetation (i.e. are agriculturally suitable) in the context of the present invention.

As is well known in the art, contact of an acidic functional group (e.g., carboxylic acid, phosphonic acid, sulfonylurea) with a base forms a salt comprising the corresponding anion derived from the acidic functional group and a positively charged counterion derived from the base. For example, a salt is formed with an amine base (e.g., pyridine, ammonia, triethylamine, isopropylamine), another organic base (e.g., a quaternary ammonium hydroxide), or an inorganic base (e.g., amides, hydrides, hydroxides, or carbonates of sodium, potassium, lithium, calcium, magnesium or barium). When a compound includes a basic function (e.g., amino or another moiety comprising a nitrogen atom with an available pair of electrons) salts can also include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

The compound of Formula 1 (6-amino-5-chloro-2-cyclopropyl-4-pyrimidinecarboxylic acid)

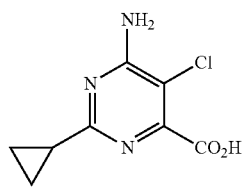

1 comprises a carboxylic acid functional group (—CO$_2$H) capable of deprotonation and forming salts with bases and also comprises an amino substituent (—NH$_2$) and pyrimidine ring nitrogen atoms with free pairs of electrons capable of protonation and forming salts with acids. Particularly useful for the present method are salts formed with bases. Of note are such salts wherein the counterion is formed from an ammonia or an amine (e.g., ammonium, dimethylammonium or isopropylammonium) or is an alkali metal cation (e.g., potassium, sodium or lithium). Particularly noteworthy for the present method are the sodium and potassium salts of the compound of Formula 1. These salts have excellent solubility in water. The potassium salt of the compound of Formula 1 is preferred, because in addition to providing excellent herbicidal efficacy for the present method, it is very water soluble, which facilitates preparation of high-strength aqueous soluble concentrate formulations, which are convenient to transport and dispense.

Fosamine (Formula 2; ethyl hydrogen (aminocarbonyl) phosphonate) comprises a half ester of a phosphonic acid functional group (—P(O)(OCH$_2$CH$_3$)OH) capable of deprotonation and forming salts with bases. Salts are more chemically stable than the free acid form of fosamine. Although a wide variety of salts of fosamine are useful in the present method, typically the ammonium salt is used, as it is available in commercial products such as KRENITE® (DuPont).

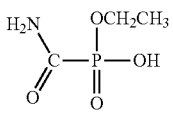

Imazapyr (Formula 3; (±)-2-[4,5-dihydro-4-methyl-4-(1-methylethyl)-5-oxo-1H-imidazol-2-yl]-3-pyridinecarboxylic acid) comprises a carboxylic acid functional group (—CO$_2$H) capable of deprotonation and forming salts with bases. Imazapyr also comprises nitrogen atoms with free pairs of electrons capable of protonation and forming salts with acids. Particularly useful for the present method are salts formed with bases. Of particular note is the isopropylammonium salt (known as imazapyr-isopropylammonium), which is commercially available in herbicide products such as ARSENAL® (BASF).

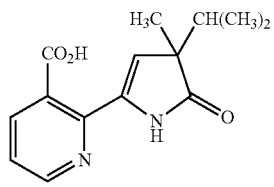

Metsulfuron-methyl (Formula 4; methyl 2-[[[[(4-methoxy-6-methyl-1,3,5-triazin-2-yl)amino]carbonyl]amino]sulfonyl]benzoate) comprises a sulfonylurea moiety (—S(O)$_2$NHC(O)N—) capable of deprotonation and forming salts with bases. Metsulfuron-methyl also comprises nitrogen atoms with free pairs of electrons capable of protonation and forming salts with acids. Particularly useful for the present method are salts formed with bases. However, metsulfuron-methyl is often used as the nonsalt form, which is commercially available in herbicide products such as ESCORT® XP (DuPont).

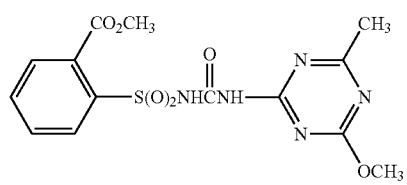

Triclopyr (Formula 5; [(3,5,6-trichloro-2-pyridyl)oxy]acetic acid) comprises a carboxylic acid functional group (—CO$_2$H) capable of deprotonation and forming salts with bases. Triclopyr also comprises a nitrogen atom with a free pair of electrons capable of protonation and forming salts with acids. Particularly useful for the present method are salts formed with bases. Of particular note is the triethylammonium salt (known as triclopyr-triethylammonium), which is commercially available in herbicide products such as GARLON® 3A (Dow AgroSciences).

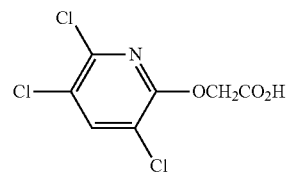

Also particularly useful as derivatives of the corresponding carboxylic acids of Formula 1 and Formula 5 (triclopyr) in the present method are ester and thioester derivatives. The carboxylic acid forms (i.e. Formulae 1 and 5) are believed to be the compounds that bind to active sites on plant enzymes or receptors causing herbicidal activity. However, ester and thioester derivatives can be transformed within the plant or the environment to the parent carboxylic acids, and therefore these derivatives also have herbicidal utility. Accordingly, ester and thioester as well as salt derivatives are useful for the present method.

Ester groups (i.e. CO$_2$R$^{AL}$) result from condensation of a carboxylic acid (CO$_2$H) with an alcohol (i.e. R$^{AL}$OH) wherein R$^{AL}$ is the radical derived from the alcohol. Thioester groups of the formula C(O)SR$^{AL}$ may be conceptually viewed as the condensation product of a carboxylic acid function with a thioalcohol (often called a mercaptan) of the formula R$^{AL}$SH. There is a wide variety of general methods known in the art for preparing carboxylic esters and thioesters from carboxylic acids.

If the radical R$^{AL}$ has more than one OH or SH function attached, the radical may be condensed with more than one carboxylic acid of Formulae 1 or 5. As these multiply esterified derivatives can be hydrolyzed to the parent carboxylic acids, these derivatives are among the ester derivatives useful for the present method. Illustrative thioester derivatives include the compounds of Formulae 1 or 5 thioesterified with alkylthiols such as methanethiol, ethanethiol or propanethiol. Illustrative ester derivatives include the compounds of Formula 1 or 5 esterified with alcohols such as methanol, ethanol, propanol, isopropanol, t-butanol, 2-methoxyethanol, 2-ethoxyethanol, 2-propoxyethanol, 2-butoxyethanol or benzyl alcohol to form methyl, ethyl, propyl, i-propyl, t-butyl, 2-methoxyethyl, 2-ethoxyethyl, 2-propoxyethyl, 2-butoxyethyl and benzyl esters, respectively.

Of the ester and thioester derivatives of the carboxylic acids of Formulae 1 and 5, the ester derivatives are of particular note, as they are generally more conveniently prepared, least expensive and most useful. Therefore illustrative as compounds from which component (a) in the present method is selected are compounds of Formula 1a, and salts thereof,

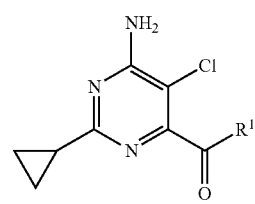

wherein
R$^1$ is OR$^2$ or SR$^3$;
R$^2$ is H, C$_1$-C$_{14}$ alkyl, C$_2$-C$_{14}$ alkoxyalkyl, C$_3$-C$_{14}$ alkoxyalkoxyalkyl, C$_2$-C$_{14}$ hydroxyalkyl or benzyl; and R³ is C₁-C₁₄ alkyl, C₂-C₁₄ alkoxyalkyl, C₃-C₁₄ alkoxyalkoxyalkyl, C₂-C₁₄ hydroxyalkyl or benzyl.

Furthermore, illustrative as compounds from which component (b4) in the present method is selected are compounds of Formula 5a, and salts thereof,

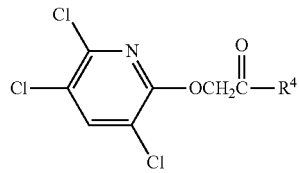

5a wherein

R⁴ is OR⁵ or SR⁶;

R⁵ is H, C₁-C₁₄ alkyl, C₂-C₁₄ alkoxyalkyl, C₃-C₁₄ alkoxyalkoxyalkyl, C₂-C₁₄ hydroxyalkyl or benzyl; and R⁶ is C₁-C₁₄ alkyl, C₂-C₁₄ alkoxyalkyl, C₃-C₁₄ alkoxyalkoxyalkyl, C₂-C₁₄ hydroxyalkyl or benzyl.

Therefore of note for the present method are compounds of Formula 1a wherein R¹ is OR² and salts thereof, and compounds of Formula 5a wherein R⁴ is OR⁵ and salts thereof, and of particular note are compounds of Formula 1a wherein R¹ is OR² and R² is C₁-C₁₄ alkyl, C₂-C₁₄ alkoxyalkyl, C₃-C₁₄ alkoxyalkoxyalkyl, C₂-C₁₄ hydroxyalkyl or benzyl, and compounds of Formula 5a wherein R⁴ is OR⁵ and R⁵ is C₁-C₁₄ alkyl, C₂-C₁₄ alkoxyalkyl, C₃-C₁₄ alkoxyalkoxyalkyl, C₂-C₁₄ hydroxyalkyl or benzyl.

For reasons of cost and herbicidal effectiveness, C₁-C₄ alkyl esters are preferred and C₁-C₂ alkyl (i.e. methyl and ethyl) esters are more preferred as esters of the compound of Formula 1. The methyl ester often provides similar efficacy in the present method at much lower application rates than the potassium salt of the compound of Formula 1. Of particular note is the 2-butoxyethyl ester of triclopyr (known as triclopyr-butotyl, which is commercially available in herbicide products such as GARLON® 4 and REMEDY® (Dow AgroSciences).

The compound of Formula 1 and its salt, ester and thioester derivatives can be prepared by the methods described in PCT publications WO 2005/063721, WO 2006/121648 and WO 2006/124657. Fosamine-ammonium is conveniently obtained in a commercial product, but this and other salts of fosamine can be prepared by the methods described in U.S. Pat. Nos. 3,627,507 and 3,846,512. Imazapyr-isopropylammonium is conveniently obtained in a commercial product, but imazapyr and its salts can be prepared by the methods described in U.S. Pat. No. 4,798,619. Metsulfuron-methyl is conveniently obtained in a commercial product, but can be prepared by the methods described in U.S. Pat. No. 4,383,113. Triclopyr is conveniently obtained in a commercial product, but can be prepared by the methods described in U.S. Pat. No. 3,862,952.

Table 1 illustrates specific compounds useful as component (a) for the present method. The following abbreviations are used in Table 1: n means normal, t means tertiary, i means iso, Me means methyl, Et means ethyl, n-Pr means n-propyl, i-Pr means isopropyl, n-Bu means butyl, t-Bu means tert-butyl, Ph means phenyl, "/" means negative formal charge, and "•" means positive formal charge.

TABLE 1

1a

| Compound Number | R¹ |
|---|---|
| 1 | —OMe |
| 2 | —OEt |
| 3 | —O—n-Pr |
| 4 | —O—i-Pr |
| 5 | —O—t-Bu |
| 6 | —OCH₂Ph |
| 7 | —O—n-Bu |
| 8 | —OCH₂CH₂CH₂OH |
| 9 | —OCH(CH₃)(CH₂)₅CH₃ |
| 10 | —OCH₂CH₂O(CH₂)₂OCH₃ |
| 11 | —OCH₂(CH₂)₆CH₃ |
| 12 | —OCH₂CH₂O(CH₂)₃CH₃ |
| 13 | —OCH₂CH(CH₂CH₃)(CH₂)₃CH₃ |
| 14 | —OCH(CH₃)CH₂O(CH₂)₃CH₃ |
| 15 | —SMe |
| 16 | —SEt |
| 17 | —S—n-Pr |
| 18 | —OH |
| 19 | —O/Li• |
| 20 | —O/Na• |
| 21 | —O/K• |
| 22 | —O/Na• |
| 23 | —O/H₄N• |
| 24 | —O/H₃N•Me |
| 25 | —O/H₃N•i-Pr |
| 26 | —O/HN•(Et)₃ |
| 27 | —O/N•(Me)₄ |
| 28 | —O/N•(Me)₃(CH₂Ph) |
| 29 | —O/S•(Me)₃ |

Formulation/Utility

In the present method, mixtures of component (a) (i.e. one or more compounds selected from the compound of Formula 1 and salts, esters and thioesters thereof) and component (b) (i.e. at least one additional herbicide selected from the group consisting of (b1) fosamine and salts thereof; (b2) imazapyr and salts thereof; (b3) metsulfuron-methyl and salts thereof; and (b4) triclopyr and ester, thioesters and salts thereof) can be formulated and applied in a variety of ways:

(1) the component (a) and component (b) compounds can be formulated separately and applied separately or applied simultaneously in an appropriate weight ratio, e.g., as a tank mix; or (2) the component (a) and component (b) compounds can be formulated together in the proper weight ratio.

Another possible combination of formulation and application includes formulating component (a) and one component (b) compound together, and applying this composition separately or simultaneously with another separately formulated component (b) compound. One skilled in the art will recognize by analogy further possible combinations of formulation and application.

For the present method, mixtures of the component (a) and component (b) compounds will generally be used as active ingredients in a composition, i.e. a formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, sorbitol, triacetin (glycerol triacetate), aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g, oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. An alkylated fatty acid liquid diluent of particular note is methylated soybean oil. Typical liquid diluents are described in Marsden, *Solvents Guide,* 2nd Ed., Interscience, New York, 1950.

The solid and liquid compositions comprising mixtures of components (a) and (b) often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for compositions comprising components (a) and (b) are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions comprising components (a) and (b) for the present method may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The component (a) and component (b) compounds are typically incorporated into compositions for the present method by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-ingredient-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", Chemical Engineering, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Table 1. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

High Strength Concentrate

| | |
|---|---|
| Compound 1 | 3.5% |
| fosamine-ammonium | 95.0% |
| silica aerogel | 0.5% |
| synthetic amorphous fine silica | 1.0% |

Example B

Wettable Powder

| | |
|---|---|
| Compound 1 | 55.7% |
| metsulfuron-methyl | 9.3% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| Compound 21 | 2.6% |
| triclopyr-triethylammonium | 7.4% |
| attapulgite granules (low volatile matter, 0.71/0.30 mm; U.S.S. No. 25-50 sieves) | 90.0% |

Example D

Extruded Pellet

| | |
|---|---|
| Compound 1 | 10.5% |
| imazapyr-isopropylammonium | 14.5% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 1 | 2.4% |
| triclopyr-butotyl | 7.6% |
| polyoxyethylene sorbitol hexoleate | 20.0% |
| $C_6$-$C_{10}$ fatty acid methyl ester | 70.0% |

Example F

Microemulsion

| | |
|---|---|
| Compound 1 | 1.2% |
| triclopyr-butotyl | 3.8% |
| polyvinylpyrrolidone-vinyl acetate copolymer | 30.0% |
| alkylpolyglycoside | 30.0% |
| glyceryl monooleate | 15.0% |
| water | 20.0% |

Test results show that the method of the present invention is remarkably effective for controlling undesired vegetation of subfamily Mimosoideae including *Acacia* species such as huisache and *Prosopis* species such as honey mesquite, even at low application rates. Control of undesired vegetation includes killing or injuring the vegetation or reducing its growth. In the context of the present method, control typically includes completely killing the treated vegetation to permanently remove it as a competitor of desirable vegetation for water, nutrients, sunlight and growing space. Mixtures of compounds of component (a) with the compounds of component (b) have been discovered to provide a synergistic effect producing complete kill for long-term control. Furthermore the present method is useful for killing not only young plants of subfamily Mimosoideae but also established plants many years old, which can be otherwise difficult to control by conventional herbicide treatments or mechanical removal. Typically the present method is used to selectively control (e.g., kill) undesired Mimosoideae plants in grasslands including pastures and rangelands. However, the present method can also be used to control Mimosoideae plants in other areas in which they are not desired.

As mixtures of the compounds of components (a) and (b) have both preemergent and postemergent herbicidal activity, to control undesired vegetation by killing or injuring the vegetation or reducing its growth, the mixtures can be usefully applied by a variety of methods involving contacting a herbicidally effective amount of a mixture, or a composition comprising the mixture and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation. Component (a) and component (b) can be applied simultaneously or consecutively to provide the mixtures.

Although mixtures of the components (a) and (b) can be applied to the soil surrounding Mimosoideae plants, the root zone of established Mimosoideae plants can extend downwards many meters, and both the quantity of surrounding soil and the depth diminish the effect of soil application. Therefore typically for the present method, mixtures of components (a) and (b) are applied to foliage of the undesired vegetation. Foliage application ensures that substantial percentages of the herbicidal active ingredients are absorbed into the plants. The compound of Formula 1 and to a greater or lesser extent the compounds of component (b) are capable of translocation to other parts of the plants.

For foliar application typically an application volume is selected that is sufficient to wet all of the Mimosoideae foliage at the desired application rate of active ingredient with relatively little drip or run off. For optimal absorption of the applied herbicidal mixture, the Mimosoideae plants should be leafed out (i.e. foliage includes leaves as well as branches and stems), and preferably the plants are actively growing. The herbicidal efficacy of foliar-applied spray mixtures is often enhanced by addition of adjuvants such as surfactants (e.g., wetting agents) and oils (e.g., methylated seed oils, vegetable oils (i.e. oils obtained from seeds and fruits) and diesel fuel oil (including mixtures thereof)). Of note as adjuvants are vegetable oils and particularly methylated seed oils such as methylated rapeseed oil and methylated soybean oil (i.e. methyl soyate). Of particular note is methyl soyate. Vegetable oils and methylated seed oils are typically added to spray mixtures in an amount of about 0.1 to about 5, more typically about 0.5 to about 2, and most typically about 1 percent by volume. Mixtures of components (a) and (b) can be applied to the foliage of Mimosoideae using a wide variety of known procedures and equipment for foliar application. These include hydraulic handgun sprayers, boom sprayers, and sprayers for aerial application from fixed wing and rotor aircraft.

For the present method, a mixture of component (a) with component (b1) (i.e. fosamine and salts thereof) is typically applied in a weight ratio of component (a) to component (b1) in the range of about 1:45 to 1:14, more typically in the range of about 1:36 to 1:20, and most typically in the range of about 1:32 to 1:22. A mixture of component (a) with component (b2) (i.e. imazapyr and salts thereof) is typically applied in a weight ratio of in the range of about 1:2.4 to 1:0.2, more typically in the range of about 1:1.8 to 1:0.8, and most typically in the range of about 1:1.6 to 1:1. A mixture of component (a) with component (b3) (i.e. metsulfuron-methyl and salts thereof) is typically applied in a weight ratio in the range of about 1:0.4 to 1:0.03, more typically in the range of about 1:0.3 to 1:0.1 and most typically in the range of about 1:0.22 to 1:0.15. A mixture of component (a) with component (b4) (i.e. triclopyr and esters, thioesters and salts thereof) is typically applied in a weight ratio in the range of about 1:4 to 1:0.8, more typically in the range of about 1:3.2 to 1:1.6, and most typically in the range of about 1:2.8 to 1:2. The above described ratios based on equivalent weights of the compound of Formula 1, fosamine, imazapyr, metsulfuron-methyl and triclopyr. For example, when component (a) is the methyl ester of the compound of Formula 1, the equivalent weight is calculated by multiplying the weight of the methyl ester by the formula weight of the compound of Formula 1 and then dividing the multiplication product by the formula weight of the methyl ester. As another example, when component (b1) is fosamine-ammonium, the equivalent weight is calculated by multiplying the weight of the fosamine-ammonium (i.e. the ammonium salt of fosamine) by the formula weight of fosamine and then dividing the multiplication product by the formula weight of the ammonium salt.

A herbicidally effective amount of the mixture comprising components (a) and (b) as well as any additional herbicides is determined by a number of factors. These factors include: formulation selected, method of application, amount and type of vegetation present, growing conditions, etc. In general, a herbicidally effective amount of the mixture comprising components (a) and (b) is applied according to the present method at an application rate in the range from about 50 g/ha to about 20 kg/ha. One skilled in the art can easily determine the herbicidally effective amount necessary for the desired level of control of undesired Mimosoideae vegetation.

One skilled in the art can also readily determine amounts of components (a) and (b) for the desired level of herbicidal control of undesired Mimosoideae vegetation, including amounts providing noticeable synergism (i.e. synergistically effective amounts), which occurs over a wide range of application rates, including application rates at which components separately provide little control. When a mixture comprising component (a) and component (b) is directed to foliage of Mimosoideae (i.e. foliage application) according to the present method, component (a) (i.e. the compound of Formula 1 and salts, esters and thioesters thereof) is typically applied at an application rate in the range of about 25 to about 1200 g/ha, more typically in the range of about 50 to about 600 g/ha, and most typically in the range of about 100 to about 300 g/ha, the weight calculated as the equivalent weight of the Formula 1 compound. Component (b1) (i.e. fosamine and salts thereof) is typically applied at an application rate in the range of about 900 to about 24000 g/ha, more typically in the range of about 1800 to about 12000 g/ha, and most typically in the range of about 3600 to about 6800 g/ha, the weight calculated as the equivalent weight of fosamine. Component (b2) (i.e. imazapyr and salts thereof) is typically applied at an application rate in the range of about 25 to about 2000 g/ha, more typically in the range of about 50 to about 1000 g/ha, and most typically in the range of about 100 to about 500 g/ha, the weight calculated as the equivalent weight of imazapyr. Component (b3) (i.e. metsulfuron-methyl and salts thereof) is typically applied at an application rate in the range of about 5 to about 350 g/ha, more typically in the range of about 10 to about 175 g/ha, and most typically in the range of about 20 to about 90 g/ha, the weight calculated as the equivalent weight of metsulfuron-methyl. Component (b4) (i.e. triclopyr and esters, thioesters and salts thereof) is typically applied at an application rate in the range of about 50 to about 4500 g/ha, more typically in the range of about 100 to about 2200 g/ha, and most typically in the range of about 200 to about 1100 g/ha, the weight calculated as the equivalent weight of triclopyr. The area (i.e. ha) in the above application rates refers to the ground area under the treated foliage.

Although mixtures comprising components (a) and (b) are typically applied according to the present method without other active ingredients, they can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of components (a) and (b) with other herbicides can broaden the spectrum of activity against additional weed species, and suppress the proliferation of any resistant biotypes. Thus the mixtures applied according to the present method can also comprise not only components (a) and (b), but also at least one additional biologically active compound or agent. The other biologically active compounds or agents can be formulated in compositions comprising at least one of a surfactant, solid or liquid diluent. For mixtures of the present invention, one or more other biologically active compounds or agents can be formulated together with components (a) and (b) to form a premix, or one or more other biologically active compounds or agents can be formulated separately from components (a) and (b), and the formulations combined together before application (e.g., in a spray tank) or, alternatively, applied in succession.

A mixture of one or more of the following herbicides with components (a) and (b) may provide further improved control of Mimosoideae vegetation: acetochlor, acifluorfen and its sodium salt, aclonifen, acrolein (2-propenal), alachlor, alloxydim, ametryn, amicarbazone, amidosulfuron, aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clefoxydim, clethodim, clodinafop-propargyl, clomazone, clomeprop, clopyralid, clopyralid-olamine, cloransulam-methyl, CUH-35 (2-methoxyethyl 2-[[[4-chloro-2-fluoro-5-[(1-methyl-2-propynyl)oxy]phenyl] (3-fluorobenzoyl)amino]-carbonyl]-1-cyclohexene-1-carboxylate), cumyluron, cyanazine, cycloate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, fluorochloridone, fluoroxypyr, flurtamone, fluthiacet-methyl, fomesafen, foramsulfuron, glufosinate, glufosinate-ammonium, glyphosate and its salts such as ammonium, isopropylammonium, potassium, sodium (including sesquisodium) and trimesium (alternatively named sulfosate), halosulfuron-methyl, haloxyfop-etotyl, haloxyfop-methyl, hexazinone, HOK-201 (N-(2,4-difluorophenyl)-1,5-dihydro-N-(1-methylethyl)-5-oxo-1-[(tetrahydro-2H-pyran-2-yl)-methyl]-4H-1,2,4-triazole-4-carboxamide), imazamethabenz-methyl, imazamox, imazapic, imazaquin, imazaquin-ammonium, imazethapyr, imazethapyr-ammonium, imazosulfuron, indanofan, iodosulfuron-methyl, ioxynil, ioxynil octanoate, ioxynil-sodium, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thio esters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, molinate, monolinuron, naproanilide, napropamide, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiocarbazil, topramezone, tralkoxydim, tri-allate, triasulfuron, triaziflam, tribenuron-methyl, tridiphane, trietazine, trifloxysulfuron, trifluralin, triflusulfuron-methyl, tritosulfuron and vernolate. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butyl.) Butyl. and *Puccinia thlaspeos* Schub.

Components (a) and (b) can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual, 13th Edition*, C. D. S. Tomlin, Ed., British Crop Protection Council, Farnham, Surrey, U.K., 2003 and *The BioPesticide Manual,* 2nd Edition, L. G. Copping, Ed., British Crop Protection Council, Farnham, Surrey, U.K., 2001.

For embodiments where one or more of these various additional mixing partners are used, the weight ratio of these various mixing partners (in total) to component (a) and (b) in total is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by mixtures of component (a) and (b) alone.

In certain instances, combinations of a mixture of component (a) and (b) with other biologically active (particularly herbicidal) compounds or agents (i.e. active ingredients) can result in a greater-than-additive (i.e. synergistic) effect on weeds and/or a less-than-additive effect (i.e. safening) on forage grasses or other crops or desirable plants. Reducing the quantity of active ingredients released in the environment while ensuring effective pest control is always advantageous. Ability to use greater amounts of active ingredients to provide more effective weed control is also advantageous. When synergism of herbicidal active ingredients occurs on weeds at application rates giving agronomically satisfactory levels of weed control, such combinations can be advantageous for reducing the cost of growing forage or other crops and decreasing environmental load. When safening of herbicidal active ingredients occurs on desirable plant species growing in the vicinity of undesired Mimosoideae vegetation, such combinations can be advantageous for increasing production of the desirable plant species by reducing weed competition.

Mixtures comprising components (a) and (b) as the only active ingredients have been discovered to typically provide excellent control of undesired Mimosoideae vegetation at application rates causing little or no injury to forage grasses of pastures and rangelands, particularly when the application of the mixtures is directed at the foliage of the Mimosoideae vegetation. However, in some situations, such as for control of undesired Mimosoideae vegetation in crops other than forage grasses, mixtures comprising not only components (a) and (b), but also a herbicide safener can be advantageous. For example, mixtures comprising components (a) and (b) can also be used in combination with herbicide safeners such as allidochlor, benoxacor, BCS (1-bromo-4-[(chloromethyl) sulfonyl]benzene), cloquintocet-mexyl, cyometrinil, cyprosulfonamide, dichlormid, 4-(dichloroacetyl)-1-oxa-4-azospiro[4.5]decane (MON 4660), 2-(dichloromethyl)-2-methyl-1,3-dioxo lane (MG 191), dicyclonon, dietholate, fenchlorazole-ethyl, fenclorim, flurazole, fluxofenim, furilazole, isoxadifen-ethyl, mefenpyr-diethyl, mephenate, methoxyphenone ((4-methoxy-3-methylphenyl)(3-methylphenyl) methanone), naphthalic anhydride (1,8-naphthalic anhydride) and oxabetrinil to increase safety to certain crops. Antidotally effective amounts of the herbicide safeners can be applied at the same time as mixtures of components (a) and (b), or applied as seed treatments. Antidotally effective amounts of safeners can be easily determined by one skilled in the art through simple experimentation.

Of note is the present method wherein the mixture of comprising components (a) and (b) further comprises at least one other herbicidal active ingredient. Of particular note is such a method where the other herbicidal active ingredient has different site of action from the compounds of components (a) and (b). In certain instances, a combination with at least one other herbicidal active ingredient having a similar spectrum of control but a different site of action will be particularly advantageous for resistance management.

The following Tests demonstrate the control efficacy of mixtures comprising component (a) and component (b) against Mimosoideae weed species. The weed control afforded by the compounds is not limited, however, to these species. In these Tests, Compound 1 is identified in Table 1 and is also recognized as the methyl ester of the compound of Formula 1 (i.e. methyl 6-amino-5-chloro-2-cyclopropyl-4-pyrimidine-carboxylate).

Biological Examples of the Invention

Test A

A field study was conducted to evaluate the efficacy of 250 g/ha of Compound 1, 6.7 kg/ha of fosamine-ammonium (i.e. ammonium salt of fosamine), 280 g/ha of imazapyr (provided in the form of the isopropylammonium salt of imazapyr) and 42 g/ha of metsulfuron-methyl, separately and in combination, for controlling a natural stand of huisache (*Acacia farnesiana*) on a ranch in southeastern Texas. Compound 1 was in the form of a wettable granule formulation containing 80% by weight of Compound 1. Fosamine-ammonium was provided by KRENITE® S, which is a water-soluble liquid formulation containing 41.5% of fosamine-ammonium. Imazapyr was provided by ARSENAL®, which is a water-soluble liquid formulation containing 28.7% of imazapyr-isopropylammonium (equivalent to 22.6% of imazapyr, i.e. imazapyr acid equivalent). Metsulfuron-methyl was provided by ESCORT® XP, which is a wettable granule formulation containing 60% of metsulfuron-methyl.

The trial design was a large block, single replicate field study using rectangular test plots measuring 12.8 m by 22.9 m. The huisache trees in the test plots averaged 2.4 m tall and were estimated to be approximately 20 years old. The formulated herbicides were diluted with water and 1% by volume of methylated seed oil was added to provide about 27.4 L of spray mixture. The treatments were applied in early autumn using a high-volume handgun sprayer projecting the spray mixture upward and across a plot in a slow back and forth motion while traversing the plot lengthwise. This produced a rainfall-like spray covering both the huisache trees and ground between trees in the plots. The volume of spray mixture used (corresponding to 935 L/ha) was sufficient to thoroughly wet the foliage of the huisache trees with relatively little drip or run off under the trees.

The effects of the herbicide treatments were visually evaluated. At 62 days after application (DAA), the percentage of defoliation in comparison to a control plot was observed. Then at 229, 543, 656 and 745 days after application % control was calculated based on the percentage of trees showing no green foliage or regrowth. The results are listed in Table A.

TABLE A

Control of Huisache using Compound 1, fosamine, imazapyr and metsulfuron-methyl, applied alone and in combination.

| Application rate (g ai/ha) | | | | % | % Control | | | |
|---|---|---|---|---|---|---|---|---|
| Compound 1 | Fosamine (*) | Imazapyr (**) | Metsulfuron-methyl | Defoliation 62 DAA | 229 DAA | 543 DAA | 656 DAA | 745 DAA |
| 250 | — | — | — | 100 | 91 | 46 | 55 | 33 |
| — | 6688 | — | — | 75 | 0 | 0 | 0 | 0 |
| — | — | 280 | — | 70 | 9 | 0 | 0 | 0 |
| — | — | — | 42 | 85 | 11 | 0 | 0 | 0 |
| 250 | 6688 | — | — | 100 | 100 | 95 | 95 | 93 |
| 250 | — | 280 | — | 100 | 95 | 100 | 100 | 100 |
| 250 | — | — | 42 | 100 | 100 | 79 | 74 | 85 |

(*) Applied as the ammonium salt. Application rate is based on the ammonium salt of fosamine.

(**) Applied as the isopropylammonium salt. Application rate is based on the imazapyr acid equivalent.

Table A shows that an application rate of 250 g ai/ha of Compound 1 provided 100% defoliation of huisache. Although at 229 DAA 91% of the huisache trees still lacked green foliage, at 543 and 656 DAA observed control diminished to around 50%, and at 745 DAA to 33%, which indicates that many of the huisache trees lacking green foliage at 229 DAA were actually not completely moribund or dead. The ratings at more than one year after herbicide application, i.e. 543, 656 and 745 DAA, are representative of long-term control of huisache from the treatment. At the application rates applied, fosamine, imazapyr and metsulfuron-methyl provided less defoliation than Compound 1, and moreover gave no long-term control of huisache. Remarkably however, combinations of Compound 1 with fosamine, imazapyr or metsulfuron-methyl synergistically provided much better long-term control of huisache. Although the Colby Equation can be used to calculate the expected response, it is not needed in this instance because the % control of fosamine, imazapyr and metsulfuron-methyl are all 0 at 543, 656 and 745 DAA, and thus the expected effect of the mixtures is just the effect of Compound 1 alone: 46% at 543 DAA, 55% at 656 DAA and 33% at 745 DAA. The much greater control provided by the mixtures demonstrates strong synergy.

Test B

A field study was conducted to evaluate the efficacy of 125 g/ha of Compound 1 and 280 g/ha of triclopyr (in the form of the butoxyethyl ester of triclopyr, i.e. triclopyr-butotyl), separately and in combination, for controlling natural stands of honey mesquite (*Prosopis glandulosa*) on ranches in western Texas. Compound 1 was in the form of an 80% wettable granule formulation. Triclopyr was provided by GARLON® 4 or REMEDY®, which are emulsifiable concentrate formulations containing 44.3% or 61.6% of triclopyr-butotyl, respectively.

The trial design was a large block, single replicate test. Each test used rectangular test plots measuring 3 m by 9 m and incorporating at least 10 mesquite plants per plot. The formulated herbicides were diluted with water, and 1% by volume of methylated seed oil was added, to provide volumes of spray mixtures corresponding to a rate of 94 L/ha at Site 1 and 140 L/ha at Site 2. The treatments were applied using flat fan nozzles on an elevated spray boom moved across the plots by an all-terrain vehicle or small tractor. The elevated spray boom and relatively low spray volumes simulated aerial (e.g., helicopter or fixed wing aircraft) applications.

In each plot 10 mesquite trees were identified with a metal tag for evaluation. The effects of the herbicide treatments were evaluated 12 months after application at Site 1 and 10 months after application at Site 2. Visual evaluations were used to rate the herbicidal effect of the various treatments. A tree was considered alive if any foliage was present within the tree canopy area or if any new growth (i.e. sprouts) emerged from the base of the tree. Control results were calculated as a percent of dead trees in each plot, e.g., 6 dead trees and 4 live trees gives a 60% control rating.

Expected results were calculated using the Colby Equation. Colby's equation (S. R. Colby, "Calculating Synergistic and Antagonistic Responses of Herbicide Combinations," *Weeds*, 15(1), pp 20-22 (1967)) calculates the expected additive effect of herbicidal mixtures, and for two active ingredients is of the form:

$$P_{a+b} = P_a + P_b - (P_a P_b / 100)$$

wherein $P_{a+b}$ is the percentage effect of the mixture expected from additive contribution of the individual components, $P_a$ is the observed percentage effect of the first active ingredient at the same use rate as in the mixture, and $P_b$ is the observed percentage effect of the second active ingredient at the same use rate as in the mixture.

For mixtures comprising Compound 1 plus triclopyr, the expected herbicidal effect was calculated based on Compound 1 alone providing observed herbicidal effect $P_a$ and triclopyr providing observed herbicidal effect $P_b$ in the Colby Equation.

Observed and expected results are listed in Table B.

TABLE B

Control of Honey Mesquite using Compound 1 and triclopyr, applied alone and in combination.

| Application rate (g ai/ha) | | % Control | | | |
|---|---|---|---|---|---|
| | | Site 1 | | Site 2 | |
| Compound 1 | Triclopyr (*) | Observed | Expected () | Observed | Expected () |
| 125 | — | 60 | — | 60 | — |
| — | 280 | 0 | — | 30 | — |
| 125 | 280 | 90 | 60 | 100 | 72 |

(*) Applied as the butotyl ester of triclopyr. Application rate is based on the triclopyr acid equivalent.
(**) Calculated using the Colby Equation.

Table B shows that 125 g/ha of Compound 1 provided only partial (i.e. 60%) long-term control of honey mesquite. Triclopyr at 280 g/ha provided little (i.e. 30% at Site 2) or no (i.e. 0% at Site 1) long-term control of honey mesquite. Remarkably, the combination of Compound 1 with triclopyr at these application rates provided excellent (i.e. 90 to 100%) control, which furthermore was much greater than the 60 to 72% control expected from additive effects.

What is claimed is:

1. A method for controlling undesired vegetation of subfamily Mimosoideae comprising applying to the undesired vegetation or its environment a herbicidally effective amount of a mixture comprising (a) one or more compounds selected from the compound of Formula 1 and salts, esters and thioesters thereof:

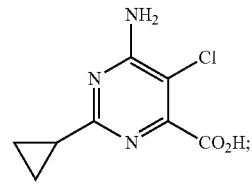

and (b) at least one additional herbicide selected from the group consisting of (b1) fosamine and salts thereof;

(b2) imazapyr and salts thereof;

(b3) metsulfuron-methyl and salts thereof; and (b4) triclopyr and esters, thioesters and salts thereof.

2. The method of claim 1 wherein the undesired vegetation comprises at least one species of genus *Prosopis*.

3. The method of claim 1 wherein the undesired vegetation comprises at least one species of genus *Acacia*.

4. The method of claim 1 wherein the mixture is applied to the foliage of the undesired vegetation.

5. The method of claim 1 wherein at least one herbicide of component (b) is selected from (b1) fosamine and salts thereof.

6. The method of claim 1 wherein at least one herbicide of component (b) is selected from (b2) imazapyr and salts thereof.

7. The method of claim 1 wherein at least one herbicide of component (b) is selected from (b3) metsulfuron-methyl and salts thereof.

8. The method of claim 1 wherein at least one herbicide of component (b) is selected from (b4) triclopyr and esters, thioesters and salts thereof.

* * * * *